United States Patent [19]

Bennett

[11] Patent Number: Plant 5,407

[45] Date of Patent: Feb. 26, 1985

[54] MINIATURE ROSE PLANT—PUCKER UP

[76] Inventor: Cecilia L. D. Bennett, 489 Minot Ave., Chula Vista, Calif. 92010

[21] Appl. No.: 525,453

[22] Filed: Aug. 22, 1983

[51] Int. Cl.[3] ..... A01H 5/00

[52] U.S. Cl. ..... Plt./10

[58] Field of Search ..... Plt./10

*Primary Examiner*—Robert E. Bagwill

[57] ABSTRACT

The subject of the present disclosure is a new and distinct variety of miniature rose plant, named 'Pucker Up', which is characterized by its blooms of bright Oriental Red with an occasional dark blush of Chrysanthemum Crimson and its exceptionally good form.

1 Drawing Figure

1

The present invention relates to a new and distinct variety of a hardy, dwarf, bush plant of the miniature class; the variety being primarily characterized as an orange-red.

The variety is further characterized by:

Long stemmed blooms of exceptionally good 'hybrid tea-type' form, borne primarily one to a stem but on occasion in sprays of 3 to 5 or more. The blooms are held very erect and well above the foliage.

Has a slight fragrance.

The plant ranges in height from 12 to 18 inches. The canes are sturdy and erect with moderate branching and medium to heavy foliage covering. The plant is a moderate to heavy bloomer that does well either outdoors or in the green house.

The plant has good growth habits, well shaped and attractive, bearing numerous leaflets of average size.

The seed parent was Futura (U.S. Plant Pat. No. 3,569), and the pollen parent was Avandel (U.S. Plant Pat. No. 4,366).

Subsequent to the origination of the variety, I have successfully reproduced it at Tiny Petals Nursery located at aforesaid retaining the distinguishing characteristics through succeeding propagations by cuttings.

The descriptive matter which follows pertains to roses grown and color values observed in plants and newly opened blooms in the months of July and August. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Pucker Up', the following is a detailed description thereof in outline; all major color plate identifications being by reference to The British Colour Council Horticultural Colour Chart, except where common terms of color definition are employed.

Type: Hardy, dwarf, bushy, green house or outdoor, exhibition quality or garden decorative potted plant.

Class: Miniature.

Variety name: Pucker Up.

Flowers borne: Usually one to a stem, but occasionally in sprays of 3 to 5 or more on erect stems with the foliage well below the blooms.

Quantity of bloom: Moderate to heavy both outdoors or green house grown.

Bud:

*Penduncle.*—Medium to long (30 to 50 mm; average diameter and sturdy; near Pod Green (061 to 061/1 page 120) with occasional light tinting of bronze.

Hairs.—Extremely small and numerous; located over the entire surface of peduncle, calyx and sepals.

*Calyx.*—Color is near Pod Green (061 to 061/1 page 120).

*Opening.*—Opens well in all weather.

Bloom:

*Size when fully open.*—Average for a miniature variety (35 to 45 mm).

*Petalage.*—Double — Averaging about 20 to 25 petals, arranged regularly, plus petaloids (3 to 5 or more).

*Form.*—Urn-shaped to ovoid as the bloom progresses. The petals remain at first somewhat tightly cupped with the tips and/or margins reflexed outward, becoming at maturity more loosely cupped; and the outermost petals reflexing more tightly as the bloom matures with the margins rolling under in a soft curl, forming a peak at the apex of the petals.

Petals: Fairly thick with good substance; 'velvet' finish on the upper surface and matte finish on the under surface of all petals. Shape — Outer petals are of a broad obovate form with a slight peak at the apex. The intermediate petals are very much like the outer petals only narrower. The inner petals are more like broad lanceolates, and the petaloids are small lanceolates and occasionally irregular in form.

Color: Newly opened flowers form plants grown outdoors (July and August 1983), Chula Vista, Calif.

*Outside petals.*—Upper Surface — Near Orient Red (819 through 819/2 page 165) from the margin to ⅔ of the petal; near Signal Red (719 to 719/1 page 93) at the lower portion of the petal with a very small area at the base of white. Occasionally the margin and even some of the body of the petal may have an overlay or blush of near Chrysanthemum Crimson (824 page 169).

*Under surface.*—Near Orient Red (819 through 819/2 page 165) with a very small area at the base of white. Darker in appearance to the upper surface because of the matte finish.

*Intermediate and inner petals.*—Very much like the outside petals except that the Signal Red may occupy a greater part of the petals, and the overlay or blush of Chrysanthemum Crimson is less prevalent.

*General color effect.*—Newly opened flowers — Brilliant Orient Red with the appearance of velvet, enhanced even more by the occasional dark shadowing of the Chrysanthemum Crimson overlay. Three days open — No fading. Five to seven days — Slight fading and some 'quilling' of the outermost petals. Spent petals drop off cleanly.

*Flower longevity.*—(August 1983) Plant in pot 4 to 7 days from bud with sepals down to fully opened bloom. Holding at fully open with only slight fading for an additional 3 to 4 days before bloom begins to drop petals. Cut blooms at livingroom temperature 4 to 5 days or longer.

Reproductive organs:

*Stamens.*—A generous amount arranged uniformly around the pistil.

*Filaments.*—Varying in length; pink color that is present even at the head of the stamen.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seed.*—Few or none.

*Sepals.*—Permanent; spear-shaped; open as the bloom opens, but does not recurve against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Ranging from near Scheeles Green (860 to 860/2 page 175) to near Spinach Green (0960 to 0960/3 page 187) with occasional bronzing of the margins and newer foliage. The upper surfaces have a satiny finish, and the under surfaces have a matte finish of a slightly lighter shade than the upper surfaces.

*Rachis.*—Medium strength; upper surface is grooved with very small hairs over the length of it. Under surface also contains some small hairs and a few small thorns as well.

*Stipules.*—Varying in length from small to medium; average width; tapering auricles angled outward at about 45 degrees.

Growth:

*Habit.*—Dwarf; bushy; average height for a miniature rose plant.

*Growth.*—Moderate.

*Canes.*—Medium; sturdy; held very erect.

*Main stems.*—Color — Ranging from near Scheeles Green (860 to 860/1 page 175) to near Spinach Green (0960 to 0960/3 page 187) with occasional bronzing, especially noticeable on the newer stems.

*Thorns.*—Averaging 15 to 20 per 10 cm on the main stems, and slightly fewer on the branches. Reddish in color with some bronzing. Small to average in size. Slender; straight or slightly hooked downward.

*Branches.*—Color — Same as main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant named 'Pucker Up' of hardy, dwarf, moderate growth, attractive appearance, substantially as illustrated and described, characterized by its blooms of brilliant Orient Red with velvety petals, enhanced occasionally by an overlay of Chrysanthemum Crimson, easy to propagate form cuttings, with flowers borne usually one to a stem, but occasionally in sprays of 3 to 5 or more.

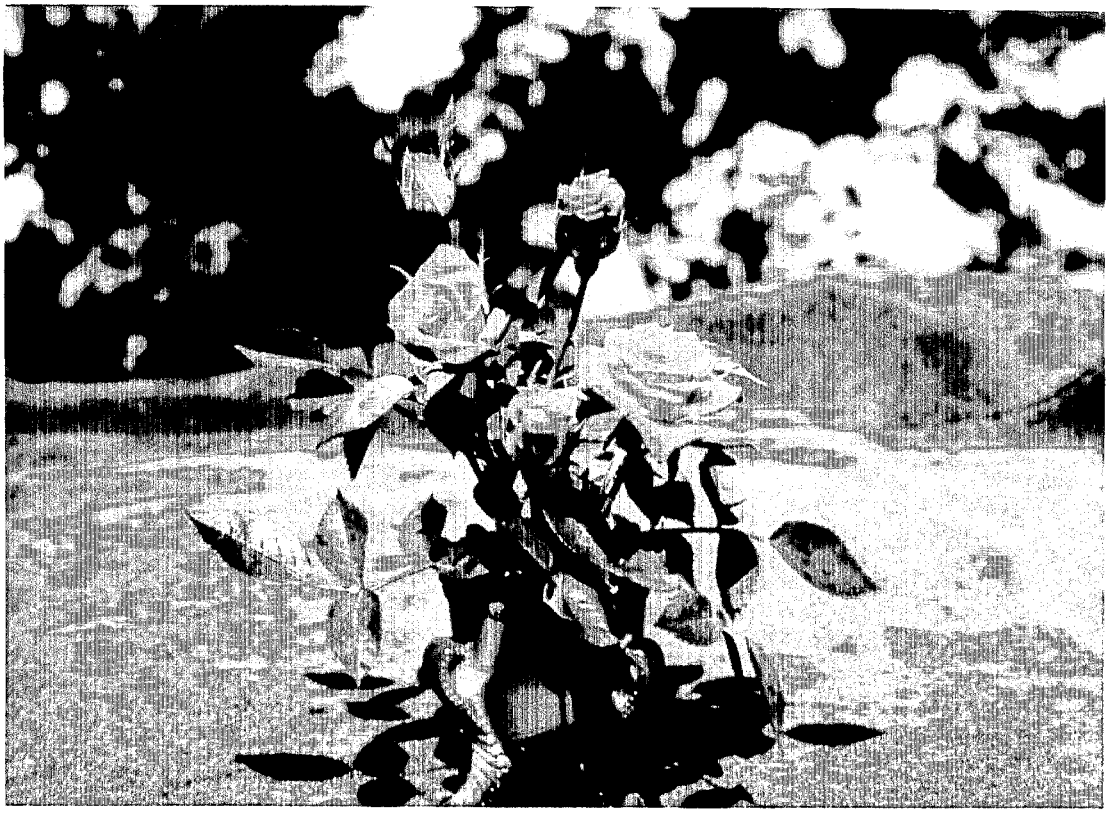

* * * * *